United States Patent [19]

Urich et al.

[11] 4,139,822

[45] Feb. 13, 1979

[54] EDDY CURRENT PROBE FOR INSPECTING INTERIORS OF GAS TURBINES, SAID PROBE HAVING PIVOTAL ADJUSTMENTS AND A BORESCOPE

[75] Inventors: Robert H. Urich, Greer, S.C.; Maurice A. Freeman, Burnt Hills, N.Y.

[73] Assignee: General Electric Company, Schenectady, N.Y.

[21] Appl. No.: 806,544

[22] Filed: Jun. 14, 1977

[51] Int. Cl.² .......................................... G01R 33/12
[52] U.S. Cl. .................................................. 324/219
[58] Field of Search ............................. 324/219–221, 324/226, 237, 238, 240, 260, 262; 73/623, 633, 637, 640; 74/99, 88, 25

[56] References Cited

U.S. PATENT DOCUMENTS

| | | | |
|---|---|---|---|
| 3,153,286 | 10/1964 | Buisson | 74/99 |
| 3,949,292 | 4/1976 | Beaver et al. | 324/220 |
| 3,990,301 | 11/1976 | Smith | 324/262 |

FOREIGN PATENT DOCUMENTS 624719  1/1961  Canada ................................. 324/237

*Primary Examiner*—Robert J. Corcoran
*Attorney, Agent, or Firm*—Jerome C. Squillaro

[57] ABSTRACT

An eddy-current crack detection probe is described which allows inspection of turbomachinery parts of conductive material for cracks without removal of the parts to be inspected from the machine or disassembly of the casings normally restricting physical access to these parts. The crack detection probe is particularly useful for field inspections of the trailing edges of turbine buckets of a gas turbine for cracks not readily detectable by optical techniques. The probe, which is insertable through a small opening in the turbomachine casing and thereafter can be remotely manipulated to assume an appropriate inspection position, includes a small eddy-current sensor and may include a borescope for remote viewing of the sensor and turbine bucket edge to be inspected.

5 Claims, 6 Drawing Figures

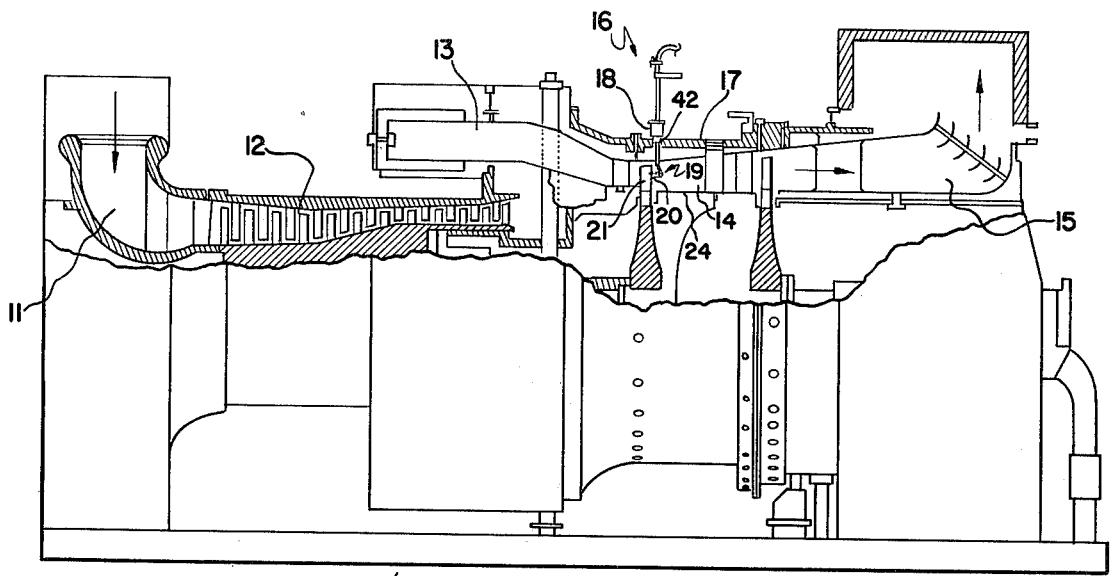
Fig. 1
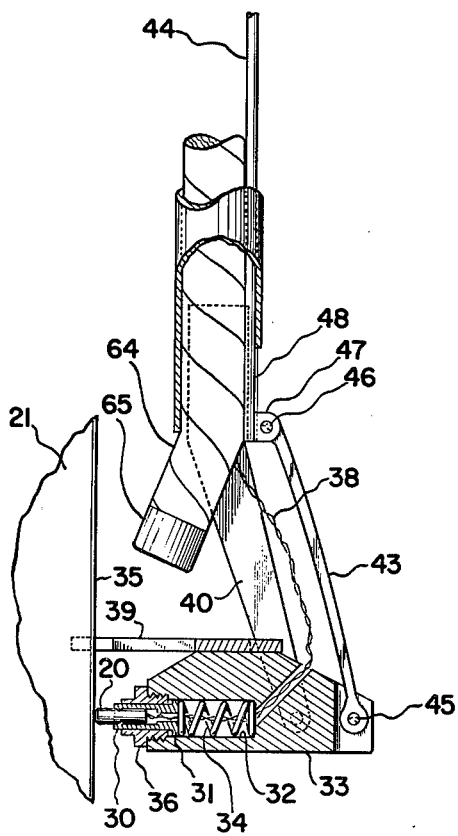
Fig. 4
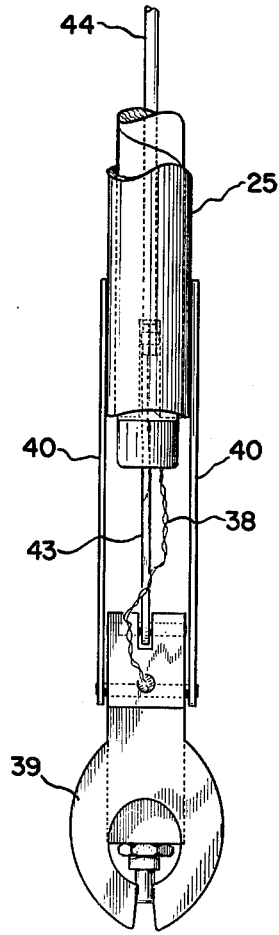
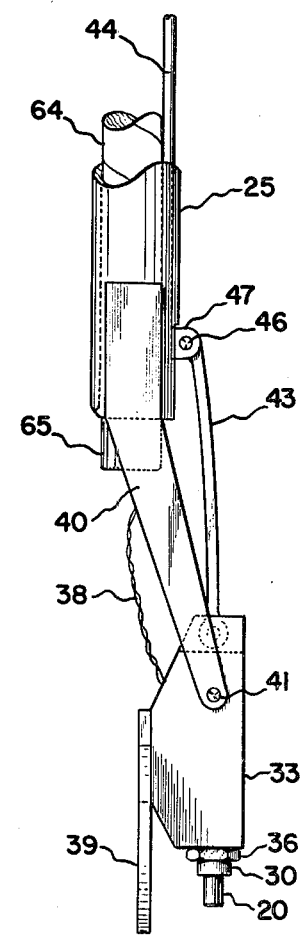

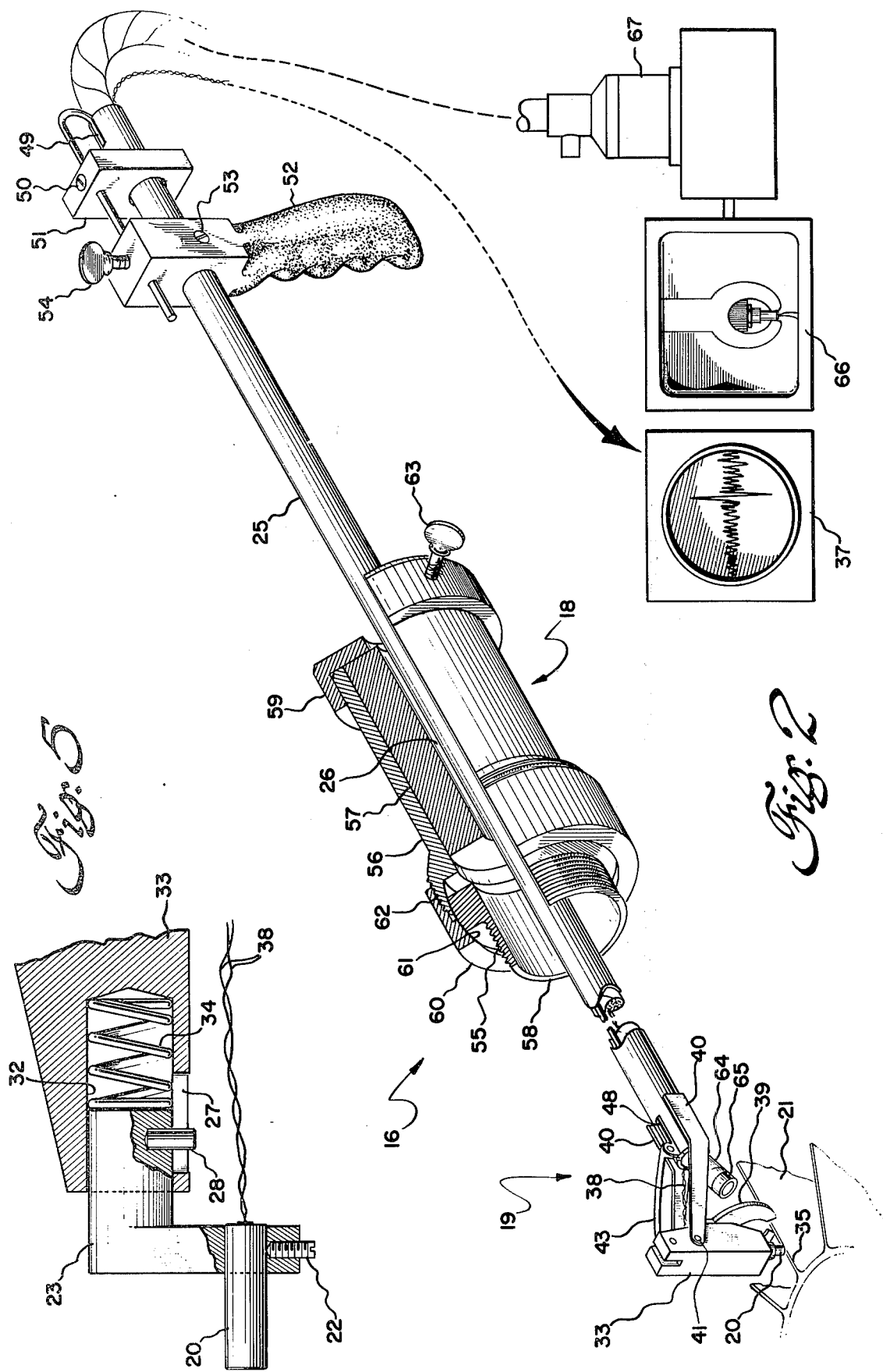

EDDY CURRENT PROBE FOR INSPECTING INTERIORS OF GAS TURBINES, SAID PROBE HAVING PIVOTAL ADJUSTMENTS AND A BORESCOPE

BACKGROUND OF THE INVENTION

This invention relates to crack detection in turbomachinery components and in particular to inspection of gas turbine buckets for cracks using an eddy-current sensor without disassembly of the gas turbine.

Inspection of turbomachinery components such as rotating gas turbine blades for cracks which may have developed during service operation has previously been performed either by partial disassembly of the machine and use of fluorescent penetrant tests, i.e., by examining under ultraviolet light parts which have been treated with fluorescent dye penetrants, or by inserting an optical borescope through the casing of the machine and viewing the resulting transmitted images of the inspected part on a screen located outside the machine. The dye penetrant method, though accurate, requires costly and timeconsuming disassembly of major portions of the gas turbine to gain access to the parts to be inspected and thus is economically unattractive for use in the field or on a frequent basis. The borescope approach, though relatively convenient for field application, is limited in that the optical nature of borescopes make them incapable of detecting minute or sub-surface cracks, which are not visible even under several powers of magnification but whose detection may be vital to prevention of severe damage to the machine.

Accordingly it is a general object of the invention to provide an improved apparatus for inspecting turbomachinery components for cracks and more particularly to provide a crack detection probe which will permit inspection of gas turbine parts without disassembly of the gas turbine.

A further object of the invention is to provide a simple, compact, remotely operable crack detection probe capable of accurately detecting minute cracks in gas turbine buckets without disassembly of the turbine casings.

SUMMARY OF THE INVENTION

A probe is provided which includes a small eddy-current sensor for detection of cracks in turbomachinery components such as gas turbine buckets. The crack detection probe is insertable into the gas flow area of the turbine through a small opening in the turbine case and thereafter can be remotely erected, positioned, and operated, thus eliminating the need for disassembly of the turbine casings to gain physical access to the buckets to be inspected. In a preferred embodiment the crack detection probe also includes a flexible borescope used for viewing the sensor and adjacent area to ensure accurate positioning of the sensor, a guide shoe to ensure proper seating of the sensor as it is moved along the area being inspected, and a support housing assembly which supports the probe and allows axial, angular, and rotational positioning movement of the probe.

BRIEF DESCRIPTION OF THE DRAWINGS

While the specification concludes with claims particularly pointing out and distinctly claiming the subject matter regarded as the invention, the invention will be better understood from the following description taken in connection with the accompanying drawings in which:

FIG. 1 is a side elevation, with parts broken away to expose internal details, of a gas turbine showing the crack detection probe of the invention in position to inspect the trailing edge of a turbine bucket;

FIG. 2 is a perspective view, with parts broken away to expose internal details, of the crack detection probe in position to inspect the edge of a bucket and also shows a camera, cathode ray tube, and eddy-current instrument associated with the probe;

FIG. 3A is a partial front elevation view showing details of the probe head assembly and its pivot connections to a yoke which in turn is connected to one end of the main body member of the probe and showing the probe sensor head in a position parallel to the longitudinal axis of the probe for insertion into the turbine gas path;

FIG. 3B is a partial side elevation view of the portion of the probe shown in FIG. 3A with the probe rotated 90° about its longitudinal axis;

FIG. 4 is a partial side elevation view, with parts broken away to expose internal details, of the probe head assembly and connections as in FIG. 3B with the head rotated to an erect position so that the eddy-current sensor of the probe head is substantially perpendicular to the surface to be inspected and with the borescope moved into position for viewing the sensor; and FIG. 5 is a side elevation view, with parts broken away to expose internal details, of a portion of the probe sensor head showing an alternate arrangement for mounting the sensor on the head.

DETAILED DESCRIPTION OF THE INVENTION

A typical inspection environment for the eddy-current crack detection probe of the invention is illustrated in FIG. 1, which shows a gas turbine 10 comprising in general an inlet 11, a compressor 12, a combustor 13, a turbine 14, and an exit 15. In the application illustrated, the eddy-current crack detection probe 16 is shown secured to turbine outer casing 17 by means of support housing assembly 18 with the probe head assembly 19 and eddy-current sensor 20 in position to inspect the trailing edge of turbine bucket 21 for possible cracks.

Now with reference to FIG. 2, which shows the probe in considerable detail, the eddy-current probe indicated generally at 16 includes an elongated main body member 25 which is slidably carried within a bore 26 of a support housing assembly 18, and a head assembly 19 which is pivotally carried by the main body member 25 at one end thereof.

The head assembly 19, whose internal details are best shown in FIG. 4, includes an eddy-current sensor 20 secured by suitable means such as crimping to a cartridge-shaped shell member 30 having an enlarged rim 31. The shell member 30 is slidably received within a bore 32 formed in a sensor head 33, and means such as spring 34 are provided within the bore 32 to resiliently urge the sensor 20 away from the head 33 towards the surface of the workpiece 21 to be inspected such as the trailing edge 35 of a turbine bucket 21. The shell member 30 is retained within the bore by a bushinng 36 that engages the shell rim 31 and is threadably or otherwise suitably secured to the head 33.

An alternate arrangement for attaching the sensor 20 to the sensor head 33 is shown in FIG. 5 wherein the sensor 20 is secured as by retaining screw 22 to an L- shaped member 23, the L-shaped member 23 in turn slidably carried within the bore 32 of sensor head 33 and slidably secured from dropping out of the head 33 by means of slot 27 and retaining screw 28. In this arrangement the sensor 20 is offset from the head 33, which facilitates inspections of portions of turbine blade edges near the inner casing 24 (see FIG. 1) of the turbine 14 by eliminating possible interference between the probe head 33 and the inner casing 24.

The eddy-current sensor 20, whose principles are known and do not form part of the present invention, includes a small coil (not shown) electrically connected to an eddy-current instrument 37 (see FIG. 2) which supplies an alternating current to the coil and receives a sensor output signal through electrical lead wires 38. A suitable eddy-current instrument 37 is Nortec NDT6D sold by the Nortec Company. The alternating current supplied to the coil develops a pulsating magnetic field around the coil, which, when applied to a nearby conductive material such as a nickel-base superalloy used in turbine buckets, induces eddy currents in the material. Changes in the induced eddy currents caused by breaks in the material (such as cracks) in turn alter the impedance of the coil, producing detectable changes in sensor output signal as suggested by the spike of the signal trace of eddy-current instrument 37 shown in FIG. 2. A recorder (not shown) such as a Gould 220 Brush Recorder may be used in conjunction with the eddy-current instrument 37 to measure output signals from the eddy-current instrument 37.

The head assembly 19 may also include a guide member or shoe 39 which is rigidly attached to the head 33. The shoe 39 extends from the head 33 substantially parallel to the sensor 20 and acts to align the sensor with, and guide it along, the surface or edge 35 to be inspected during a crack inspection traverse.

The head 33 of the eddy-current crack detection probe 16 is pivotally connected to a yoke 40, as at 41, for rotation between a first position, as shown in FIGS. 3A and 3B, wherein the head assembly 19 may be easily inserted through a small access hole 42 in the turbine outer casing 17 and a second position, as shown in FIGS. 2 and 4, wherein the head 33 is positioned to inspect a workpiece such as the trailing edge 35 of turbine bucket 21.

To rotate or pivot the head 33 between its first position of FIGS. 3A and 3B and its second position of FIGS. 2 and 4, suitable means such as a link 43 and a rod 44 are provided. Link 43 is pivotally connected at one end through pivot connection 45 to the head 33, and is pivotally connected at its other end through pivot connection 46 to ear or lug 47 which protrudes from the end of rod 44.

The main body member 25, through which rod 44 extends, is preferably tubular and of annular cross section, and at the end connected to the head assembly 19 has a slot 48 through which lug 47 extends. At the other end of the tubular main body member 25, rod 44 exits the member 25 through slot 49 and is bent back and secured by means such as screw 50 to trigger block 51, which is slidably mounted on the main body member 25. The rod 44 may extend beyond the block 51 and slidably engage a handle or grip 52 rigidly secured to main body member 25 as by screw 53. Locking means such as thumbscrew 54 may be provided for securing rod 44 to grip 52 and thus locking head 33 in position.

The support housing assembly 18, shown in detail in FIG. 2, is formed with a bore or passage 26 sized to slidably receive the tubular main body member 25 and is suitably adapted to be secured to outer casing 17 of the apparatus to be inspected as by threads 55. In a typical construction the support housing assembly 18 is cylindrical and comprises an outer housing 56, coaxial inner support barrel 57 and support clamp 58, and end rings 59 and 60. The support clamp 58 includes threaded end 55 which allows the housing assembly 18 to be secured to the casing 17 in cooperation with threaded access hole 42, and spherical surface 61 which engages a mating split bearing surface formed by bottom end ring 60 and outer housing 56. When assembly 18 is secured to casing 17 by clamp 58, the spherical surface 61 of support clamp 58 allows rotation of all parts of probe 16 except fixed support clamp 58 about the longitudinal axis of the probe and angular movement of the probe relative to the typically radial direction of access hole 42. Further flexibility in positioning the probe 16 relative to the workpiece 21 is provided by forming the bore 26 of the support housing assembly 18 eccentric relative to the axis of the cylindrical support barrel 57 and support clamp 58. Threaded connection 62 between outer housing 56 and bottom end ring 60 permits, by suitable tightening thereof, locking of probe 16 against further rotation and angular movement. Top ring 59 and thumbscrew 63 allow locking or adjustment of sliding friction between tubular main body member 25 and the support housing assembly 18.

A flexible borescope 64 extending through main body member 25 may also be provided for viewing the eddy-current sensor 20 and adjacent area to ensure accurate positioning of the sensor 20 and to scan areas of the workpiece 21 of particular interest, for example, areas warranting detailed or multiple inspections. Position of the optical end 65 of borescope 64 may be varied (by means not shown), e.g., the end may be set in a retracted position aligned with the longitudinal axis of the probe 16 during insertion as illustrated in FIGS. 3A and 3B, then moved into viewing position as shown in FIG. 4. The image received by the borescope 64 may be transmitted to a cathode ray tube or television monitor 66 by means of a low light level television camera 67, a monitoring arrangement which reduces inspector fatigue which could result from viewing through the borescope eyepiece.

In use, the probe elements are first arranged so that the head 33 is in its first position, i.e., aligned parallel to the longitudinal axis of the tubular main body member 25 as shown in FIGS. 3A and 3B, then the head assembly end of the probe is inserted through access hole 42 into the gas path of the turbine 14. After the support housing assembly 18 is secured to outer casing 17 by the threaded end 55 of support clamp 58, thumbscrew 54 of trigger 52 is loosened and trigger block 51 is pushed towards trigger 52 which, by means of rod 44 and link 43, rotates head 33 into its second position substantially perpendicular to the surface of the workpiece 21 to be inspected for cracks. After thumbscrew 54 is tightened, locking head 33 in its inspection position, further adjustments, if necessary, are made in axial, circumferential and angular position of the eddy-current sensor 20 by means of rotation of the probe on spherical surface 61 and sliding of the main body member 25 in the bore 26 of support housing assembly 18. After final positioning of the sensor 20 is complete, thumbscrew 63 is tightened, outer housing 56 is tightened in end ring 60, and the flexible borescope 64 is moved into position as shown in FIGS. 2 and 4. The borescope 64 and eddy-current instrument 37 are activated, and inspection of the workpiece for cracks then proceeds.

The crack detection probe described above has been found particularly useful in detecting cracks as small as 0.060 inch in the trailing edge region of turbine buckets of material IN 738, a commercial nickel-base superalloy. Because removal of gas turbine casings and disassembly of major components have been obviated by use of this probe, it is estimated that several thousand dollars and several weeks may be saved in a single field inspection of the turbine blades of a gas turbine.

While there has been shown and described what is considered a preferred embodiment of the invention, it is understood that various other modifications may be made therein. It is intended by the appended claims to claim this and other such modifications which fall within the true spirit and scope of the present invention.

What is claimed is:

1. An eddy-current crack detection probe for inspecting a turbine bucket of conductive material disposed within a casing of an assembled turbine without disassembly of said turbine, said probe comprising:

an elongated hollow tube;

an eddy-current sensor pivotably connected to said elongated hollow tube adjacent one end thereof, said sensor movable between a first position permitting insertion of said sensor through a small opening in said casing and a second position permitting inspection of said turbine bucket for the presence of cracks;

a yoke, said yoke rigidly attached to and extending from one end of said hollow tube, and having a yoke pivot axis for pivotably securing said sensor within said yoke;

means for remotely moving said sensor from said first position to said second position and from said second position to said first position, said means for remotely moving said sensor including a rod axially slidable within said tube and a link member pivotally connected at one end to said rod and at the other end to said sensor in a manner such that movement of said rod along its axis will cause rotation of said sensor about said yoke pivot axis, and a borescope carried within said hollow tube and adapted to allow remote viewing of said eddy-current sensor and the turbine bucket to be inspected to ensure accurate positioning of said sensor and to scan portions of said turbine bucket of particular interest.

2. The probe of claim 1 further including a guide member adapted to engage an edge of said turbine bucket when said sensor is in said second position to align and guide said sensor with and along said edge.

3. The probe of claim 2 further including a sensor head for carrying said eddy-current sensor, said sensor head having a spring for yieldingly urging said sensor away from said head in response to pressure from the surface of the workpiece contacted by the sensor during inspection thereof.

4. The probe of claim 3 further including a support housing assembly having a bore therethrough for slidably carrying said hollow tube, said support housing assembly having means for securing said housing assembly to the casing of an assembled turbine with said sensor head extending through a small opening in said casing, and means for permitting rotational, axial, and angular movement of said hollow tube with respect to its longitudinal axis after said housing assembly has been secured to said casing.

5. The probe of claim 4 further including an eddy-current instrument for furnishing a signal to said sensor and processing an output signal therefrom; wire means forming an electrical connection between said sensor and said eddy-current instrument and extending internally through said hollow tube; and a television monitor and television camera optically connected to said borescope for remote viewing of said sensor and the turbine bucket to be inspected.

* * * * *